United States Patent [19]

Snyders

[11] Patent Number: 5,256,132
[45] Date of Patent: Oct. 26, 1993

[54] CARDIAC ASSIST ENVELOPE FOR ENDOSCOPIC APPLICATION

[76] Inventor: Robert V. Snyders, 31 W. Brentmoor, Clayton, Mo. 63105

[21] Appl. No.: 930,985

[22] Filed: Aug. 17, 1992

[51] Int. Cl.$^5$ .............................................. A61M 1/12
[52] U.S. Cl. ...................................... 600/16; 128/64; 600/37
[58] Field of Search .................. 128/64; 600/16, 17, 600/18, 37; 623/3

[56] References Cited

U.S. PATENT DOCUMENTS

| | | | |
|---|---|---|---|
| 2,826,193 | 3/1958 | Vineberg | 128/64 |
| 3,034,501 | 5/1962 | Hewson | 128/64 |
| 3,053,249 | 9/1962 | Smith | 128/64 |
| 3,455,298 | 7/1969 | Anstadt | 128/64 |
| 3,668,708 | 6/1972 | Tindal | 623/3 |
| 4,048,990 | 9/1977 | Goetz | 128/64 |
| 4,536,893 | 8/1985 | Parravicini | 128/64 |
| 4,690,134 | 9/1987 | Snyders | 128/64 |
| 5,131,905 | 7/1992 | Grooters | 600/16 |
| 5,169,381 | 12/1992 | Snyders | 600/16 |

Primary Examiner—William E. Kamm
Assistant Examiner—George Manuel
Attorney, Agent, or Firm—Polster, Lieder, Woodruff & Lucchesi

[57] ABSTRACT

A cardiac assist envelope for endoscopic application to permit the anatomic insertion of the envelope through an endoscopic cannula in which the body of the envelope is formed of a flexible but inelastic material and has form shaping spring elements embedded in the material to allow for folding of the envelope for endoscopic insertion and spring back of the material to a configuration necessary for cardiac assist function through a single driver conduit with shuttle gas flow divisions.

9 Claims, 1 Drawing Sheet

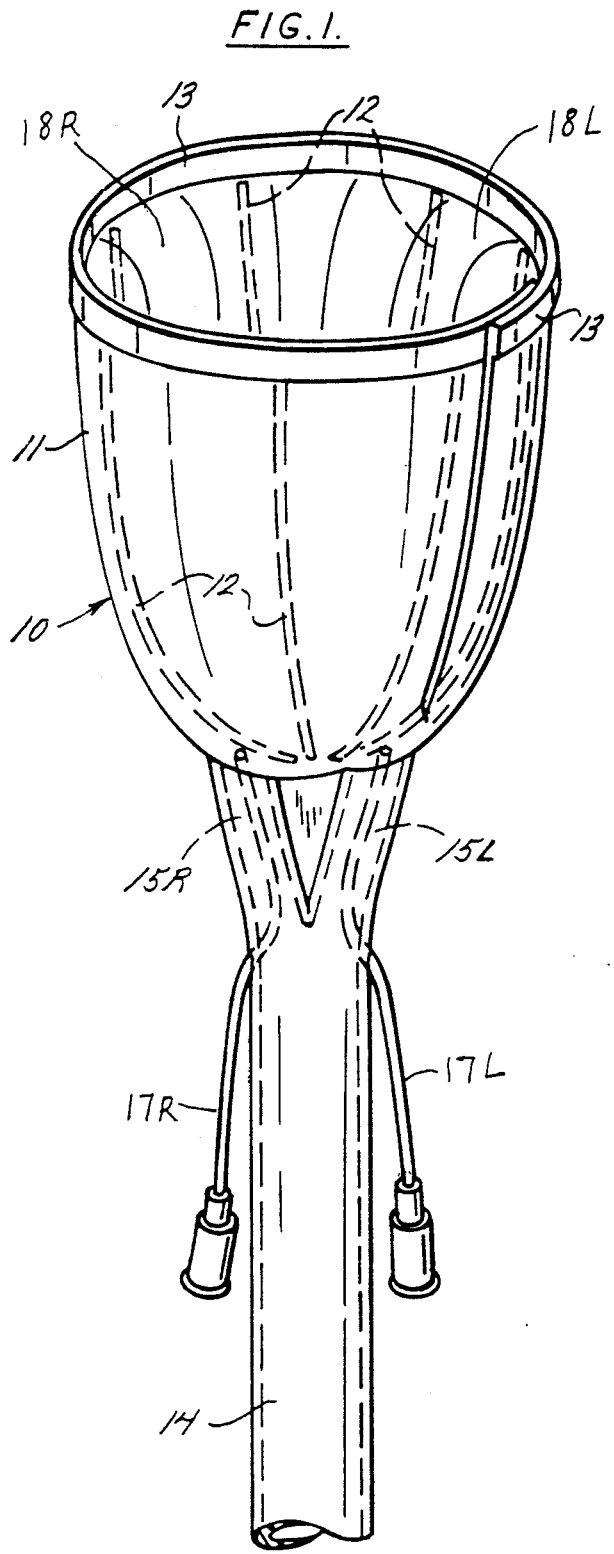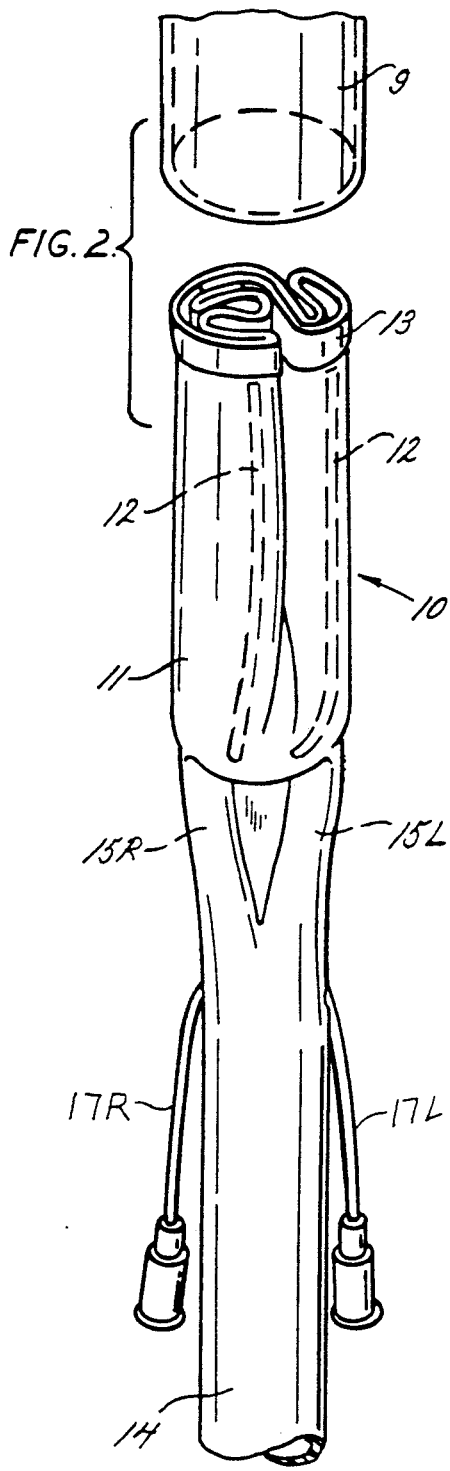

CARDIAC ASSIST ENVELOPE FOR ENDOSCOPIC APPLICATION

BACKGROUND OF THE INVENTION

1. Field of the Invention.

This invention is particularly concerned with modifying the ventricular assist heart envelope to permit its anatomic insertion through an endoscopic cannula with video guidance to achieve a much less traumatic experience than placement via an open heart surgical procedure.

2. Description of the Prior Art.

The prior art known in respect of devices to apply resuscitating and massaging action to a human heart include Vineberg 2,826,193 of Mar. 11, 1953; Hewson 3,034,501 of May 15, 1962; Anstadt 3,455,298 of Jul. 15, 1969; Parravicini 4,536,893 of Aug. 27, 1985; and Snyders 4,690,134 of Sept. 1, 1987. In each of these examples, the device is inserted in an open heart operation which is a traumatic experience for the patient.

More modern medical and surgical practices have begun to develop an endoscopic cannula procedure in combination with video guidance for permitting less traumatic surgical interventions.

In such devices as Vineberg or Hewson an inflatable heart massager is in the form of a flexible distendable resilient bag with inner and outer walls of differing thickness, with the outer wall being thicker to minimize distention of the device. The interior of the bag is able to be divided into chambers so each can have its own pressure fluid supply.

Another form of heart massage apparatus is shown in Goetz in 4,048,990 of Sept. 20, 1977 which has a cup shaped inflatable bladder surrounding the heart and supplied with pressure pulses. There is a basket-like support for holding the bladder in an operational position around the heart, with the basket-like support on the outside of the bladder.

It does not appear from these known items of prior art that any is suitable for application in the more modern surgical practices, such as endoscopic insertion and retrieval methods and provision of both systolic and diastolic assist features.

BRIEF SUMMARY OF THE INVENTION

This invention has as its principle objective the construction of a cardiac envelope suitable for endoscopic applications.

An important object is to be able to fold the ventricular assist device (VAD) so it can be applied in an endoscopic procedure.

With the foregoing object in mind it is another important object to form the wall of the VAD of thin fabricated material of 40-60 mil. (1 to 1 ½mm. or less) to thus afford maximum flex, fold, crimp or wrapping allowances needed for compactness to enable endoscopic cannula insertion to the endopericardial space, with the use of a cannula diameter of 20-30 mm. (¾" to 1 ¾") for the insertion.

A further object of the invention is the incorporation of a woven or Dacron or equivalent material for the VAD body wall to allow for sutural or other stabilizing means for attachment to the pericardial sac.

A further important object is the fabrication of the VAD shell wall with the lamination of thin strips of spring material, either in encircling or helical or vertical placement within an elastomer shell wall to allow for full expansion of the VAD after endoscopic passage to the endopericardial space.

A further object of the invention is directed to the fabrication of a VAD shell with an outer surface or sheath of a flexible but inelastic biomedical microporous material to avoid adhesion of the shell to adjacent surfaces, and to apply the same treatment to the heart contact surfaces of the sacs within the shell, and driver conduit means connected to the shell, such sheathing to therefore greatly facilitate device retrieval when the VAD is no longer needed.

Other objects of the invention will be set forth as the specification proceeds.

BRIEF DESCRIPTION OF THE DRAWING

A preferred embodiment of the invention is shown in the accompanying drawings, wherein:

FIG. 1 is a perspective view of the VAD in its extended position for the placement thereof around a heart; and FIG. 2 is a view of the VAD when in its folded position for entry into an endoscopic cannula.

DETAIL DESCRIPTION OF THE VAD EMBODIMENT

In the view of FIG. 1, the VAD body 10 in its normally extended position shows a thin shell wall 11 having imbedded therein a system of spring struts 12 which are intended to assure full expansion of the body 10 as shown. The open end of the body is formed with a suture collar 13 for pericardial stabilizing attachment, and a wedge 16 is formed in the side wall for purposes of obtaining a fit for the heart. The struts 12 are formed of a spring material that will show up on X-Ray. There are a number of suitable strut materials embodying nickel titanium alloy, nickel cobalt metal, or wire or ribbon in essentially flat strip form. The body 10 is formed for attachment to a driver conduit 14 which is divided at its upper end into right and left extensions 15R and 15L respectively. The driver conduit has a diameter of from 20 to 25 mm. The body 10, in the form of a tapering shell, is constructed of any one of several materials, such as a Dacron tricot, or similar woven fabric, or silicone rubber sheeting, or a similar medical grade elastomer or an equivalent material, or material formed from polytetrafluoroethylene. "The several materials which are equivalent to those specified above can be a woven fiber embedded in the silicone rubber sheeting or a similar medical grade elastomer, all to allow suturable or other attachment to adjacent host tissue, particularly the pericardial sac." The material selected should have a 40-60 mil. thickness and can be furnished by any one of current manufacturing sources, which affords a highly flexible yet inelastic enclosure wall in opposition to which an efficient sac liner distending action will occur. The sac liner is of the form shown in U.S. Pat. No. 4,690,134 and is incorporated herein by reference. The sac liners are rendered nonadhesive by being formed of a biomedical microporous material on heart contact surface.

The modification of the body shell relates to the fabrication of the spring strips 12 which can be wires of 10-20 mil. thickness and 30-50 mil. width laminated within a Dacron elastomer wall. While the strips 12 are shown in longitudinal positions which are preferred, they can include encircling or helical strips so the body 10 can assume the necessary conformation after insertion.

It is an important feature of the invention to provide a single driver conduit 14 which facilitates endoscopic VAD insertion, with shuttle gas flow divisions to right 15R and left 15L portals at the point of VAD body shell entry or simple coaptation of the gas shuttle lines. The conduit 14 is sheathed in a biomedical microporous material to prevent adhesion to adjacent surfaces.

In the drawing, the driver conduit 14 is conveniently provided with pressure monitoring lines 17R and 17L "which are located to lie outwardly of the conduit 14" to transmit the pressure conditions in the respective spaces defined by sac liners 18R and 18L depicted in FIG. 1 by the curved lines representing the surfaces which form the sac liners. The sacs are formed of the noted nonadherent material.

Thoracoscopic instrumentation currently available is used for endoscopic insertion of the VAD body 10, with utilization of video guidance and aided by accessory endoscopic apparatus clinically available, such as instruments, sutures, clips, staples, etc. The endoscopic endopericardial surgical placement of the present VAD would be either via a left sub-costal extra abdominal trans-diaphragmatic approach or a trans xiphoid extra abdominal supra-diaphragmatic approach to thus avoid left chest cavity transit by the VAD shuttle conduit, though one or more additional left chest percutaneous access sites will be needed for extra-instrumentation requirements at the time of VAD insertion and suture stabilization.

An additional benefit of the spring supported body shell 11 is the expectation of enhanced epicardial-sac interface negative pressure development during sac retraction (i.e. diastolic phase of gas shuttle movement) with the conformation feature of a strut-supported thin wall preventing wall deformation (collapse) during phasic sac retraction. Such interface negative pressure modulation will provide some measure of diastolic assistance known to be advantageous for more effective cardiac support in the myopathic dysfunctional states. The shell 10 is formed with a wedge space and the free edges of that wedge space are connected by a suturable flap lined by a microporous material that is placed in lapped position when folded.

What has been disclosed and described is a presently preferred embodiment, but it is to be understood that modifications and variations may come to mind without departing from the invention or its equivalents.

What is claimed is:

1. A cardiac assist envelope suitable for endoscopic applications to a human heart, said envelope comprising:
   a) a body formed of a medical grade elastomer that is highly flexible yet inelastic as an enclosure for a human heart, said body material being foldable to reduce the envelope for endoscopic applications;
   b) a system of spring strips embedded in said body in position to spread the envelope and assure conformation of said body shape to a human heart;
   c) flexible and elastic material sacs disposed in said body; and
   d) a single driver conduit connected to said sacs in said body and formed with left and right gas flow divisions.

2. The cardiac envelope set forth in claim 1 wherein said body material has a thickness of the order of 40 to 60 mil. to afford foldability upon itself to a diameter of 20 to 30 mm.

3. The cardiac envelope set forth in claim 1 wherein said body is formed with an open end opposite to said single driver conduit, and a suture collar on said open end for providing for pericardial stabilizing attachment to a human heart.

4. The cardiac envelope set forth in claim 1 wherein said system of spring strips embedded in said body consist of wires having 10–20 mil. thickness and 30–50 mil. width.

5. The cardiac envelope set forth in claim 1 wherein said body is sheathed in a nonadherent material to render its removal uneventful.

6. The cardiac envelope set forth in claim 1 wherein said body supports on its interior said flexible and elastic material sacs for receiving gas flow from said single driver conduit, said sacs enclosing separate spaces, and pressure monitor conduits connected into each of said spaces, said pressure monitor conduits having connections extending outwardly alongside said driver conduit.

7. The cardiac envelope set forth in claim 6 wherein said flexible and elastic sacs having heart contact surfaces that are nonadherent but said sacs are freely responsive to gas flow from said single driver conduit.

8. A method of preparing a cardiac envelope for anatomic endoscopic cannula application to a human heart; the method comprising:
   a) forming an envelope of a flexible and inelastic material into an open ended configuration suitable for enclosing a human heart;
   b) attaching a single driver conduit to the envelope opposite the open end;
   c) embedding spring elements in the envelope to spread the envelope into its open ended configuration to enclose a human heart; and
   d) foldably reducing the envelope to a size for passage through the endoscopic cannula.

9. A cardiac assist envelope suitable for endoscopic applications to a human heart, said envelope comprising:
   a) a body formed of a medical grade elastomer having an embedded tricot or equivalent fabric weave that is highly flexible yet inelastic as an enclosure for a human heart, said body material being foldable to reduce the envelope for endoscopic applications;
   b) a system of spring elements embedded in said body material and normally functional to expand the envelope into a configuration substantially shaped to a human heart;
   c) flexible and elastically responsive material forming right and left sacs disposed in said body for nonadhesively contacting the surfaces of a human heart; and
   d) gas flow means connected to said respective right and left sacs in said body, said gas flow means being sheathed in a biomedical material to prevent adhesion to adjacent surfaces.

* * * * *